(12) United States Patent
Van Saarloos

(10) Patent No.: US 7,682,023 B2
(45) Date of Patent: Mar. 23, 2010

(54) LIMBAL-BASED EYE TRACKING

(75) Inventor: Paul Van Saarloos, Western Australia (AU)

(73) Assignee: Customvis PLC, Balcatta (AU)

( * ) Notice: Subject to any disclaimer, the term of this patent is extended or adjusted under 35 U.S.C. 154(b) by 508 days.

(21) Appl. No.: 10/585,129

(22) PCT Filed: Dec. 31, 2004

(86) PCT No.: PCT/AU2004/001837

§ 371 (c)(1),
(2), (4) Date: Apr. 3, 2007

(87) PCT Pub. No.: WO2005/065527

PCT Pub. Date: Jul. 21, 2005

(65) Prior Publication Data

US 2008/0252849 A1 Oct. 16, 2008

(30) Foreign Application Priority Data

Jan. 9, 2004 (AU) .............................. 2004900095

(51) Int. Cl.
*A61B 3/14* (2006.01)

(52) U.S. Cl. .................. 351/209; 351/206; 351/246; 607/89; 604/294

(58) Field of Classification Search .................. 351/209
See application file for complete search history.

(56) References Cited

U.S. PATENT DOCUMENTS

| 4,812,033 | A | 3/1989 | Ishikawa |
| 5,966,197 | A | 10/1999 | Yee |
| 6,095,648 | A | 8/2000 | Birngruber et al. |
| 6,276,798 | B1 * | 8/2001 | Gil et al. ..................... 351/206 |
| 6,663,242 | B1 * | 12/2003 | Davenport .................. 351/221 |
| 2006/0200013 | A1 * | 9/2006 | Smith et al. ................. 600/319 |
| 2007/0091265 | A1 * | 4/2007 | Kardon et al. .............. 351/206 |

FOREIGN PATENT DOCUMENTS

| EP | 0397377 A1 | 11/1990 |
| EP | 0279589 B1 | 6/1991 |
| WO | WO 94/18883 A1 | 9/1994 |
| WO | WO 95/28879 A1 | 11/1995 |
| WO | WO 99/18868 A1 | 4/1999 |
| WO | WO 99/23936 A2 | 5/1999 |
| WO | WO 99/55216 A2 | 11/1999 |
| WO | WO 01/074231 A2 | 10/2001 |
| WO | WO 02/087442 A1 | 11/2002 |
| WO | WO 03/053228 A2 | 7/2003 |

* cited by examiner

*Primary Examiner*—Jessica T Stultz
(74) *Attorney, Agent, or Firm*—Stephen A. Bent; Foley & Lardner LLP

(57) ABSTRACT

A method of determining and/or tracking the position of an eye, includes utilizing at least two wavelength components of a plural wavelength zone that traverses the limbus of the eye to obtain a profile of whiteness and/or redness across the zone, and identifying from the profile at least one predetermined reference position that indicates the position of the eye. Apparatus for carrying out the method is also disclosed.

41 Claims, 2 Drawing Sheets

LIMBAL-BASED EYE TRACKING

FIELD OF THE INVENTION

This invention relates generally to the determination of the position of the eye during ophthalmic procedures, and is particularly useful for fixing and tracking eye position during ophthalmic surgery by laser ablation, which is usually carried out for refractive correction purposes.

BACKGROUND ART

Refractive correction by laser ablation has evolved into a highly customised procedure in which an accurate topographical map of the patient's eye is obtained, eg. using wavefront techniques, and a precision ablation profile predetermined to a high degree of dimensional accuracy. The ablation profile is carried out by programming the laser surgical machine to apply multiple successive laser pulses with great precision to the corneal area being treated. The pulses may be of smaller uniform cross-section but scanned over controlled ablation patterns, or of larger cross-section but masked to varying cross-sections, with or without scanning.

Whichever ablation procedure is adopted, there is a requirement that the position of the eye be known initially with great accuracy, and that, during the procedure, any movements of the eye be accurately compensated for in the aiming of the laser pulses. It will be appreciated that patients are awake during the procedure and that movements that may arise include both voluntary and involuntary movements of the eye, and head movements: any of these movements can occur even when, as is normally the case, the patient is holding a steady gaze on a fixation target. Total immobilisation of the eye is not considered practical.

The conventional approach to eye tracking in ophthalmic surgery by ablation has been to focus on the pupil as an object readily detectable in an image or from reflection patterns and to determine and track the location of the pupil's centre. Examples of this approach are provided by U.S. Pat. Nos. 5,345,281 and 5,980,513, and by international patent publication WO 00/27273, which also cites other references reliant on a pupil-based technique. U.S. Pat. No. 5,980,513 describes a system in which the treatment laser optics are employed to project an infrared sensor beam in multiple spots onto the pupil boundary, and to recover the reflected beam.

It is well recognised that a pupil varies in size with ambient light and other influences, and this is addressed by artificial dilation or by making allowance in the pattern recognition algorithms. However, what is not so well recognised is that the geometrical or mathematical centre of the pupil actually moves by up to 0.7 mm as the pupil expands and contracts in size. These shifts in the pupil centre may have been tolerable in conventional "broad-scale" ablations but are wholly unacceptable in high precision custom ablations.

The present applicant considers that the better reference point for accurate eye tracking is the limbus, the boundary between the iris and the sclera regions, because the limbus maintains a fixed relationship and a close circularity with respect to the lens of the cornea, which is of course the object of the ablation. There have been a number of patents that propose limbus-based eye tracking or position detection, including U.S. Pat. Nos. 5,865,832, 5,966,197, 6,095,648, 6,179,422, 6,299,307, 6,604,825 and 6,702,809, and US patent publication 2002/0013575. These arrangements typically involve detection of an intensity difference between light reflected from the sclera, which is of course white, and the iris, which is coloured.

It is not to be inferred that, by referring to or discussing herein specifically identified documents by number, the applicant is suggesting that these documents constitute common general knowledge.

U.S. Pat. Nos. 5,865,832, 5,966,197, and 6,702,809 disclose eye tracking systems in which the limbus is statically illuminated by lateral light sources, and a lune-shaped image of the whole limbus is projected onto a multiple element detector system. The system of U.S. Pat. No. 5,966,197 employs pairs of detectors on a pair of mutually orthogonal diameters to detect the two limbus positions on each diameter, by monitoring spatially for steps on the detected image.

U.S. Pat. No. 6,179,422 employs a different approach: instead of static illumination of the whole limbus, an illuminating beam is scanned radially across a segment of the limbus, using the same scanning optics as for the ablation beam. The scattered beam is recovered by separate optics and directed to a photo-detector that monitors for an amplitude step indicative of the limbal boundary.

It is an object of the invention to provide improved methods for determining and/or tracking the position of an eye, especially prior to and during ophthalmic laser ablation surgery.

SUMMARY OF THE INVENTION

It has been realised, in accordance with the invention, that the search/detect/comparison for the "white" against the coloured iris, the basis of several of the above mentioned references, presents a number of difficulties. Firstly, the search for white would clearly need to be defined against other colours in all lighting conditions, ie. to say the intensity of the "white" would be dependent on the lighting conditions, and a simple search for "white" will not cater for all conditions. Secondly, most subjects under surgical conditions would have a lot of red on the sclera (some cases worse than others), making the "white" even more difficult to search/detect/compare against. Thirdly, many eyes have a light coloured iris (eg. light blue), and often there are numerous red blood vessels in the limbus area. In these situations the average brightness level on each side of the limbus is very similar, making an automatic detection of limbus by this approach impossible or very difficult.

The essential concept of the invention in one aspect is to utilise the colour contrast between the iris and the sclera to detect the position of the limbus by measuring the degree of whiteness across the boundary. In another aspect, the invention utilises the greater presence of blood vessels in the sclera to detect the position of the limbus by measuring the degree of redness across the boundary.

The invention provides, in a first aspect, a method of determining and/or tracking the position of an eye, including:

utilising at least two wavelength components of a plural wavelength image of a zone that traverses the limbus of the eye to obtain a profile of whiteness and/or redness across the zone; and identifying from the profile at least one predetermined reference position that indicates the position of the eye.

The zone that traverses the limbus may be a linear zone or a larger region. Moreover, the image of the zone may be part of a larger image, eg of the whole limbus.

In an embodiment, said profile is obtained by analysing the relative intensities of the two wavelength components across said zone.

Typically, said zone extends substantially radially across the limbus.

Said at least one predetermined reference position is conveniently identified as the centre point of a segment of said zone in which said whiteness and/or redness profile has the greatest gradient.

The method preferably includes recording said plural wavelength image.

The two wavelength components are preferably in the visible light range of the electromagnetic spectrum.

Preferably, the image is a digitally recorded image, eg. a digital video record or the like image of the zone. The method advantageously utilises at least two of the three wavelength components that mix to characterise the colours of the image, eg. in an RGB (red, green, blue) colour video system.

In an embodiment the image includes the whole or substantially the whole limbus.

The method preferably further includes locating the position of the centre of the eye by determining data points comprising multiple said reference positions at spaced intervals about the limbus and then analysing these data points to locate the centre of the limbus and thereby characterise the position of the eye.

The method of the first aspect of the invention is preferably incorporated in a method of treating an eye by laser ablation, eg. for refractive correction purposes, in which the method of the invention is utilised to determine and/or track the position of the eye for the purpose of properly positioning each laser pulse.

In a second aspect, the invention provides ophthalmic laser ablation apparatus including:
- means to deliver a pulsed laser beam for performing a laser ablation procedure on an eye of a patient;
- means positionable to view and record a plural wavelength component digital image of at least a zone of the eye of the patient that traverses the limbus of the eye; and
- analysis means connected to receive said digital image and programmed to carry out the steps of the method of the first aspect of the invention and to thereby determine and/or track the position of the eye.

The zone that traverses the limbus may be a linear zone or a larger region. Moreover, the image of the zone may be part of a larger image, eg of the whole limbus.

Preferably, said means positionable to view and record a plural wavelength component digital image of at least a zone of the eye is arranged so that said region extends substantially radially across the limbus.

The apparatus of the second aspect of the invention may also be programmed to carry out each of the optional steps of the method of the first aspect of the invention.

BRIEF DESCRIPTION OF THE DRAWINGS

The invention will be further described, by way of example only, with reference to the accompanying drawings, in which.

DESCRIPTION OF PREFERRED EMBODIMENTS

Figure 1:
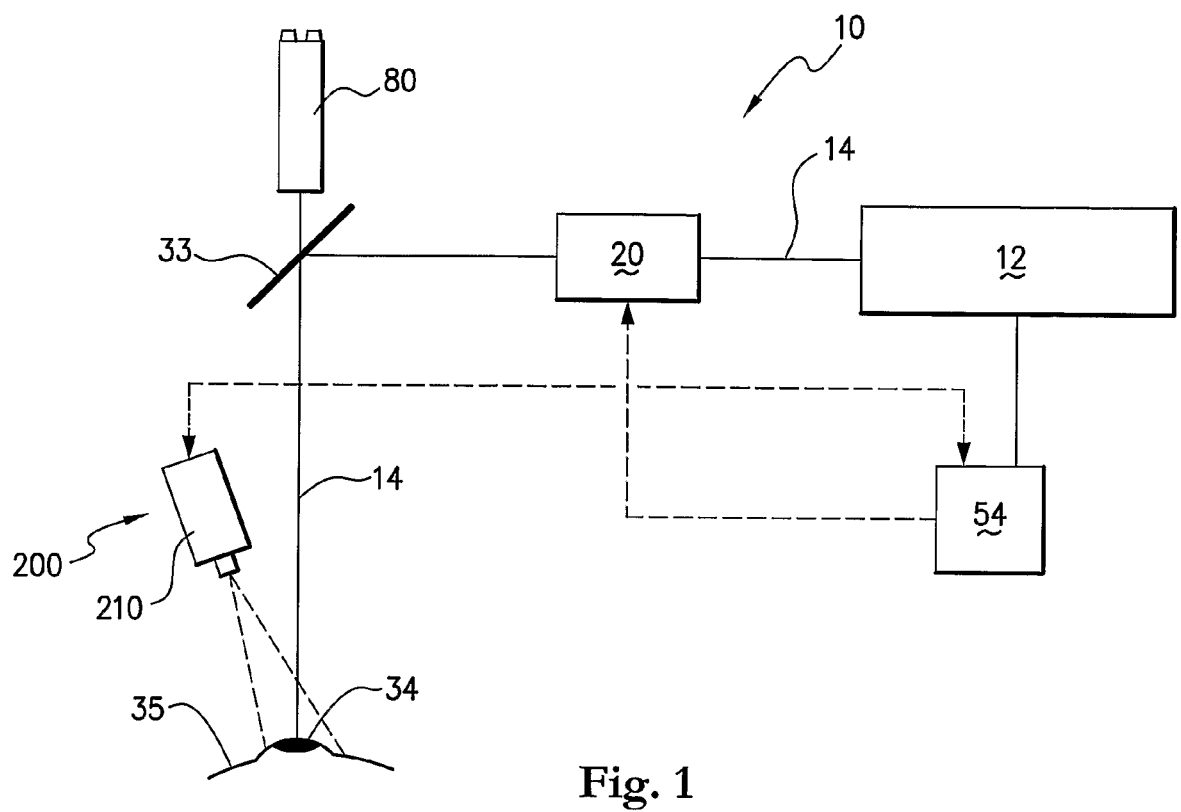
FIG. 1 is a highly schematic representation of the certain components of an ophthalmic laser ablation apparatus that incorporates a solid state laser engine and is modified and programmed for carrying out the method of the invention.

A suitable apparatus 10 (FIG. 1) for carrying out laser ablation on a patient to effect refractive correction, includes a solid state laser system 12 that emits a primary laser beam 14 of desired wavelength suitable for the laser ablation. Beam 14 is directed by a beam delivery system 20 and further optics 33 onto the cornea 34 of an eye 35 of a supine patient accommodated on a bed (not shown) forming part of the system.

Controller 54, typically a computer system, controls at least the output beam parameters of laser system 12, and the elements of the beam delivery system 70 so as to apply a customised ablation profile to each eye of the patient. A suitable microscope 80, focussed on the cornea, is provided to allow the surgeon to inspect and monitor the procedure.

Laser system 12 may contain an excimer laser, or a solid state laser such as Nd: YAG or Nd: YLF.

In order to ensure that the ablation profile is delivered with precision to the corneal surface, controller 54 must know with precision the initial position of the eye and must track the position of the eye during the procedure: any detected displacement of the cornea must be reflected either by an adjustment of the ablation profile or by suspension of the ablation. The tracking is for the purpose of detecting any lateral movement of the eye, whether voluntary or involuntary on the part of the patient, and including movement arising from movement of the head and to fire each laser pulse at the correct position.

The apparatus is accordingly fitted with an eye tracking sub-system 200. Sub-system 200 includes a miniature digital video camera 210 provided for recording a full colour image of a zone of the eye that is sufficient to indicate the whole limbus and adjacent sclera, at predetermined intervals, eg. of the order of microseconds. This camera is activated by, and delivers its digital recorded images, to the main controller 54 of the apparatus. Ideally the digital video camera views the eye co-linear to the microscope view and patient's direction of gaze.

Figure 2:
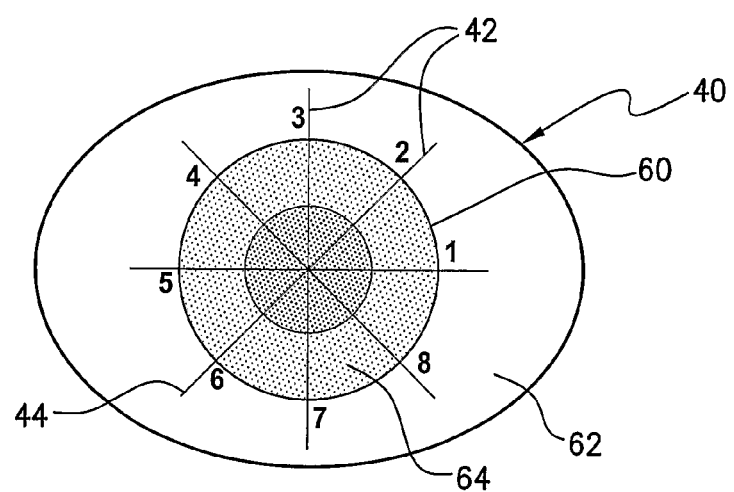
FIG. 2 is a diagrammatic front elevation of the eye with the main viewable physiological segments shown, and with a superimposed grid which, in the preferred practice of the invention, is used to find the centre of the cornea preparatory to a laser ablation treatment of the eye's cornea.

With reference to FIG. 2, the initial position of the eye is determined by controller 54, utilising image analysis techniques as follows. For each digitally recorded image of the eye, the position of the limbus 60 is determined (by means to be described shortly) on each arm 42 of a grid 40 of eight radial arms formed at 45° intervals by four crossed lines 44. Each arm is longer than a standard limbal radius, and the location of the limbus on each arm, if indeed it is found, is a respective "edge" of the monitored zone.

A score is given for the position of these edges along the arms: the closer the radius to the respective edges matches the limbal radius, the higher the score. If the grid is concentric with the centre of the eye, then edges will be expected at the limbal radius along all of the arms, and a high score will result.

Scores are taken at grid positions across the whole image, and the position of the centre of the eye is determined as grid centre where the highest score is achieved. This centre is used as a governing reference point for initiating and controlling the ablation profile applied by beam 14.

The actual positions of the limbal transitions or "edges" are determined as follows. In each region defined by an arm 42 of grid 40 extending across the limbus, the relative intensities of the primary wavelength components of the full colour image are determined. In a typical digital imaging system, these will be the RGB (red, green and blue) components. When the intensities are equal, that part of the image will be white, in this case indicating the sclera 62 (FIG. 2), whereas a high intensity of one or two of the components relative to the other(s) will indicate the coloured zone of the iris 64.

Figure 3:
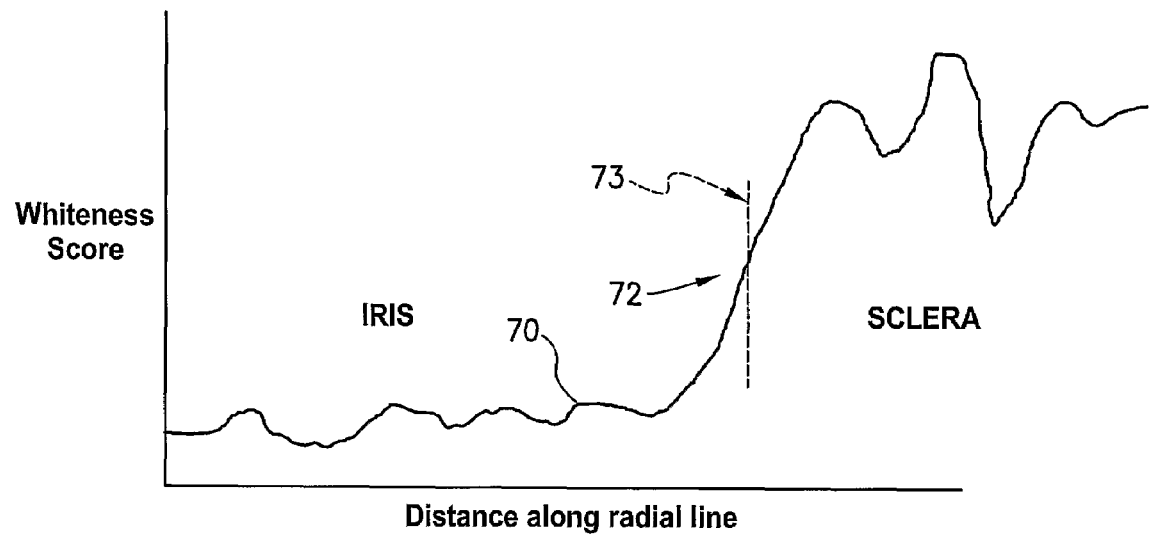
FIG. 3 is a diagram of a representative whiteness profile across a limbal boundary.

It is thus possible to produce a whiteness profile across a linear radial zone from this analysis of wavelength component intensity. An example of such a whiteness profile, 70, along a radial line across the limbus, is shown in FIG. 3. Controller 54 is programmed to select the limbal "edge" as the midpoint 73 of the zone 72 of greatest gradient in the whiteness profile curve 70.

In FIG. 3, the iris is to the left, and the sclera to the right. The greater irregularity of the whiteness profile for the sclera arises from blood vessels in the sclera greater level of blood vessels to the sclera. This reflects the greater level of blood vessels in the sclera relative to the iris. In view of this difference, the location of the limbus from the whiteness profile can be verified from analysis of the image for redness : the redness profile similarly shows a marked transition between the iris and the sclera.

Different analytic criteria are applied in the tracking of the eye during an ablation procedure. The tracking is for the purpose of detecting any lateral movement of the eye, whether voluntary or involuntary on the part of the patient, and including movement arising from movement of the head.

Figure 4:
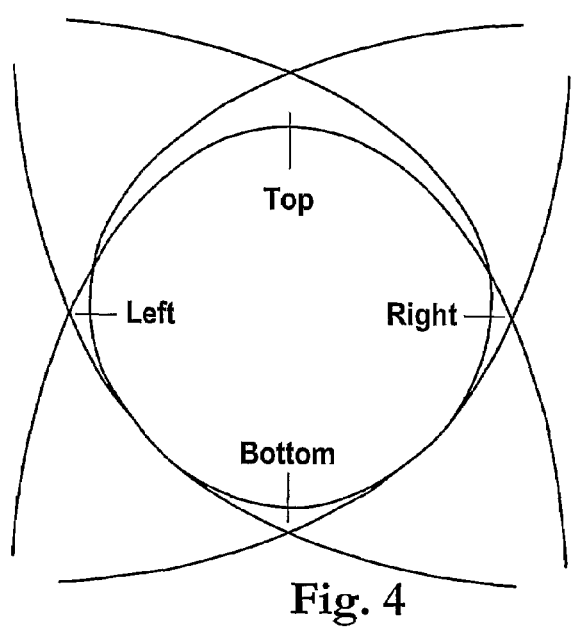
FIG. 4 is a diagram illustrating curve fits of circular or polynomial functions to accurately identify the position of the left, right upper and lower boundaries.

With reference to FIG. 4, the same grid 40 of arms 42 is used to track the eye. However, now the edges for arms in four quadrants are used to determine parabolas of best fit for four edges of the limbus. At least three points in each quadrant are necessary for a parabolic fit. This results in four turning points at the top, bottom, left and right edges of the limbus, as illustrated in FIG. 4. An algorithm is also used to eliminate any points that are determined to be outside an acceptable range.

The resulting parabolas and turning points are used to determine if the eye has been tracked, as the resulting parabolas and turning points should be within certain constraints.

If the results are acceptable the centre of the eye is determined from them, and the eye position data is applied to the ablation control algorithm. If the data is not acceptable and it does not appear that the eye is being tracked then this is also communicated, typically triggering a suspension of the ablation.

In an alternative approach, controller may track after the initial setting using circle of best fit determined from the initial location of the eye.

The invention claimed is:

1. A method of determining and/or tracking the position of an eye, including:
   utilizing at least two wavelength components of a plural wavelength image of a zone that traverses the limbus of the eye to obtain a profile of whiteness and/or redness across the zone; and
   identifying from the profile at least one predetermined reference position that indicates the position of the eye.

2. A method according to claim 1 wherein said zone is a linear zone.

3. A method according to claim 1 wherein said profile is obtained by analyzing the relative intensities of the two wavelength components across said zone.

4. A method according to claim 3 wherein said zone extends substantially radially across the limbus.

5. A method according to claim 1, wherein said at least one predetermined reference position is identified as the centre point of a segment of said zone in which said whiteness and/or redness profile has the greatest gradient.

6. A method according to claim 1, including recording said plural wavelength image prior to carrying out said utilizing and identifying steps.

7. A method according to claim 1, wherein said two wavelength components are in the visible light range of the electromagnetic spectrum.

8. A method according to claim 1, wherein said image is a digitally recorded image.

9. A method according to claim 8 wherein said image is a digital video record or like image of the zone.

10. A method according to claim 1 wherein said profile of whiteness is obtained.

11. A method according to claim 1 wherein said profile of whiteness is obtained from at least two of three wavelength components that mix to characterize the colors of the image.

12. A method according to claim 11 wherein substantially equal intensities of the wavelength components indicates the sclera, while a high intensity of one or two of the wavelength components relative to the other (s) indicates the iris.

13. A method according to claim 11 wherein said three wavelength components comprise red, green and blue (RGB) in a color video system.

14. A method according to claim 1 wherein said image includes the whole or substantially the whole limbus.

15. A method according to claim 1 further including locating the position of the centre of the eye by determining data points comprising multiple said reference positions at spaced intervals about the limbus and then analyzing these data points to locate the centre of the limbus and thereby characterized the position of the eye.

16. A method according to claim 1 incorporated in a method of treating an eye by laser ablation and utilized to determine track the position of the eye for the purpose of properly positioning each laser pulse.

17. Ophthalmic laser ablation apparatus including:
   means to deliver a pulsed laser beam for performing a laser ablation procedure on an eye of a patient;
   means positionable to view and record a plural wavelength component digital image of at least a zone of the eye of the patient that traverses the limbus of the eye; and
   analysis means connected to receive said digital image and programmed to:
   (i) utilize at least two wavelength components of a plural wavelength image of a zone that traverses the limbus of the eye to obtain a profile of whiteness and/or redness across the zone; and
   (ii) identifying from the profile at least one predetermined reference position that indicates the position of the eye.

18. Apparatus according to claim 17 wherein said zone is a linear zone.

19. Apparatus according to claim 17 wherein said profile is obtained by analyzing the relative intensities of the two wavelength components across said zone.

20. An apparatus according to claim 19 wherein said means positionable to view and record a plural wavelength component digital image of at least a zone of the eye is arranged so that said zone extends substantially radially across the limbus.

21. Apparatus according to claim 17 wherein said at least one predetermined reference position is identified as the centre point of a segment of said zone in which said whiteness profile has the greatest gradient.

22. Apparatus according to claim 17 wherein said two wavelength components are in the visible light range of the electromagnetic spectrum.

23. Apparatus according to claim 17 wherein said image is a digitally recorded image.

24. Apparatus according to claim 23 wherein said image is a digital video record or the like image of the zone.

25. Apparatus according to claim 17 wherein said analysis means is programmed to obtain said profile of whiteness.

26. Apparatus according to claim 17 wherein said profile of whiteness is obtained from at least two of three wavelength components that mix to characterized the colors of the image.

27. Apparatus according to claim 26 wherein substantially equal intensities of the wavelength components indicates the sclera, while a high intensity of one or two of the wavelength components relative to the other (s) indicates the iris.

28. Apparatus according to claim 26 wherein said three wavelength components comprise red, green and blue (kGB) in a color video system.

29. Apparatus according to claim 17 wherein said image includes the whole or substantially the whole limbus.

30. A method according to claim 2 wherein said zone extends substantially radially across the limbus.

31. A method according to claim 4, including recording said plural wavelength image prior to carrying out said utilizing and identifying steps.

32. A method according to 4 wherein said profile of whiteness is obtained from at least two of three wavelength components that mix to characterize the colors of the image.

33. A method according to claim 32 wherein substantially equal intensities of the wavelength components indicates the sclera, while a high intensity of one or two of the wavelength components relative to the other (s) indicates the iris.

34. A method according to claim 4 wherein said image includes the whole or substantially the whole limbus.

35. A method according to claim 2 incorporated in a method of treating an eye by laser ablation and utilized to determine track the position of the eye for the purpose of properly positioning each laser pulse.

36. A method according to claim 4 incorporated in a method of treating an eye by laser ablation and utilized to determine track the position of the eye for the purpose of properly positioning each laser pulse.

37. A method according to claim 32 incorporated in a method of treating an eye by laser ablation and utilized to determine track the position of the eye for the purpose of properly positioning each laser pulse.

38. An apparatus according to claim 18 wherein said means positionable to view and record a plural wavelength component digital image of at least a zone of the eye is arranged so that said zone extends substantially radially across the limbus.

39. Apparatus according to claim 20 wherein said profile of whiteness is obtained from at least two of three wavelength components that mix to characterized the colors of the image.

40. Apparatus according to claim 39 wherein substantially equal intensities of the wavelength components indicates the sclera, while a high intensity of one or two of the wavelength components relative to the other (s) indicates the iris.

41. Apparatus according to claim 20 wherein said image includes the whole or substantially the whole limbus.

\* \* \* \* \*